United States Patent
Wistrand et al.

(10) Patent No.: US 7,485,753 B2
(45) Date of Patent: Feb. 3, 2009

(54) CONTRAST AGENTS

(75) Inventors: Lars-Goran Wistrand, Oslo (NO); Mikkel Thaning, Oslo (NO); Oskar Axelsson, Oslo (NO); Sven Andersson, Lomma (SE)

(73) Assignee: GE Healthcare AS, Olso (NO)

( * ) Notice: Subject to any disclaimer, the term of this patent is extended or adjusted under 35 U.S.C. 154(b) by 241 days.

(21) Appl. No.: 11/565,673

(22) Filed: Dec. 1, 2006

(65) Prior Publication Data

US 2008/0199402 A1 Aug. 21, 2008

(30) Foreign Application Priority Data

Dec. 2, 2005 (NO) .................................. 20055702

(51) Int. Cl.
*C07C 233/58* (2006.01)
*A61K 49/04* (2006.01)
*A61K 31/16* (2006.01)

(52) U.S. Cl. ........................ 564/153; 564/133; 514/616; 424/9.451

(58) Field of Classification Search ................. 564/153, 564/133; 514/616; 424/9.451
See application file for complete search history.

(56) References Cited

U.S. PATENT DOCUMENTS

| 5,019,370 A | 5/1991 | Jay et al. |
| 5,817,873 A | 10/1998 | Meyer et al. |
| 2002/0040162 A1* | 4/2002 | Gabriel et al. .............. 564/155 |

FOREIGN PATENT DOCUMENTS

| EP | 436316 | 7/1991 |
| EP | 354836 | 1/1993 |
| EP | 782563 | 6/1999 |
| WO | 9501966 | 1/1995 |

* cited by examiner

*Primary Examiner*—Shailendra Kumar
(74) *Attorney, Agent, or Firm*—Craig Bohlken

(57) ABSTRACT

The present invention relates to iodine containing compounds containing a central cyclopropane scaffolding moiety allowing for the arrangement of three iodinated phenyl groups bound thereto.

The invention also relates to the use of such diagnostic compositions as contrast agents in diagnostic imaging and in particular in X-ray imaging and to contrast media containing such compounds.

14 Claims, No Drawings

CONTRAST AGENTS

TECHNICAL FIELD OF THE INVENTION

The present invention relates to a class of compounds and to diagnostic compositions containing such compounds where the compounds are iodine containing compounds. More specifically the iodine containing compounds are chemical compounds containing a cyclopropane scaffolding moiety allowing for the arrangement of three iodinated phenyl groups bound thereto.

The invention also relates to the use of such diagnostic compositions as contrast agents in diagnostic imaging and in particular in X-ray imaging and to contrast media containing such compounds.

DESCRIPTION OF RELATED ART

All diagnostic imaging is based on the achievement of different signal levels from different structures within the body. Thus in X-ray imaging for example, for a given body structure to be visible in the image, the X-ray attenuation by that structure must differ from that of the surrounding tissues. The difference in signal between the body structure and its surroundings is frequently termed contrast and much effort has been devoted to means of enhancing contrast in diagnostic imaging since the greater the contrast between a body structure and its surroundings the higher the quality of the images and the greater their value to the physician performing the diagnosis. Moreover, the greater the contrast the smaller the body structures that may be visualized in the imaging procedures, i.e. increased contrast can lead to increased spatial resolution.

The diagnostic quality of images is strongly dependent on the inherent noise level in the imaging procedure, and the ratio of the contrast level to the noise level can thus be seen to represent an effective diagnostic quality factor for diagnostic images.

Achieving improvement in such a diagnostic quality factor has long been and still remains an important goal. In techniques such as X-ray, magnetic resonance imaging (MRI) and ultrasound, one approach to improving the diagnostic quality factor has been to introduce contrast enhancing materials formulated as contrast media into the body region being imaged.

Thus in X-ray early examples of contrast agents were insoluble inorganic barium salts which enhanced X-ray attenuation in the body zones into which they distributed. For the last 50 years the field of X-ray contrast agents has been dominated by soluble iodine containing compounds. Commercial available contrast media containing iodinated contrast agents are usually classified as ionic monomers such as diatrizoate (marketed e.g. under the trade name Gastrografen™), ionic dimers such as ioxaglate (marketed e.g. under the trade name Hexabrix™), nonionic monomers such as iohexyl (marketed e.g. under the trade name Omnipaque™), iopamidol (marketed e.g. under the trade name Isovue™), iomeprol (marketed e.g. under the trade name Iomeron™) and the non-ionic dimer iodixanol (marketed under the trade name and Visipaque™).

The most widely used commercial non-ionic X-ray contrast agents such as those mentioned above are considered safe. Contrast media containing iodinated contrast agents are used in more than 20 millions of X-ray examinations annually in the USA and the number of adverse reactions is considered acceptable. However, since a contrast enhanced X-ray examination will require up to about 200 ml contrast media administered in a total dose, there is a continuous drive to provide improved contrast media.

The utility of the contrast media is governed largely by its toxicity, by its diagnostic efficacy, by adverse effects it may have on the subject to which the contrast medium is administered and by the ease of storage and ease of administration. Since such media are conventionally used for diagnostic purposes rather than to achieve direct therapeutic effect, it is generally desirable to provide media having as little as possible effect on the various biological mechanisms of the cells or the body as this will lead to lower toxicity and lower adverse clinical effect. The toxicity and adverse biological effects of a contrast medium are contributed to by the components of the formulation medium, e.g. the solvent or carrier as well as the contrast agent itself and its components such as ions for the ionic contrast agents and also by its metabolites.

The major contributing factors to the toxicity of the contrast medium are identified as the chemotoxicity of the contrast agent, the osmolality of the contrast medium and the ionic composition or lack thereof of the contrast medium.

Desirable characteristics of an iodinated contrast agent are low toxicity of the compound itself (chemotoxicity), low viscosity of the contrast medium wherein the compound is dissolved, low osmolality of the contrast medium and a high iodine content (frequently measured in g iodine per ml of the formulated contrast medium for administration). The iodinated contrast agent must also be completely soluble in the formulation medium, usually an aqueous medium and remain in solution during storage.

The osmolality of the commercial products, and in particular of the non-ionic compounds is acceptable for most media containing dimers and non-ionic monomers although there is still room for improvement. In coronary angiography for example, injection into the circulatory system of a bolus dose of contrast medium has caused severe side effects. In this procedure contrast medium rather than blood flows through the system for a short period of time, and differences in the chemical and physiochemical nature of the contrast medium and the blood that it replaces can cause undesirable adverse effects such as arrhythmias, QT prolongation and reduction in cardiac contractive force. Such effects are seen in particular with ionic contrast agents where osmotoxic effects are associated with hypertonicity of the injected contrast medium. Contrast media that are isotonic or slightly hypotonic with the body fluids are particularly desired. Low osmolar contrast media have low renal toxicity which is particularly desirable. The osmolality is a function of the number of particles per volume unit of the formulated contrast medium.

To keep the injection volume of the contrast media as low as possible it is highly desirable to formulate contrast media with high concentration of iodine/ml, and still maintain the osmolality of the media at a low level, preferably below or close to isotonicity. The development of non-ionic monomeric contrast agents and in particular non-ionic bis(triiodophenyl) dimers such as iodixanol (EP patent 108638) has provided contrast media with reduced osmotoxicity allowing contrast effective iodine concentration to be achieved with hypotonic solution, and even allowed correction of ionic imbalance by inclusion of plasma ions while still maintaining the contrast medium Visipaque™ at the desired osmolality (WO 90/01194 and WO 91/13636).

However, X-ray contrast media at commercial high iodine concentration have relative high viscosity, ranging from about 15 to 60 mPas at ambient temperature. Generally, contrast media where the contrast enhancing agent is a dimer has higher viscosity than the corresponding contrast media where the contrast enhancing agent is the monomer corresponding to the dimer. Such high viscosities pose problems to the administrators of the contrast medium, requiring relatively large bore needles or high applied pressure, and are particularly pronounced in pediatric radiography and in radiographic techniques which require rapid bolus administration, e.g. in angiography.

X-ray contrast agents of high molecular weight has been proposed, e.g. polymers with substituted triiodinated phenyl groups grafted on the polymer, see EP 354836, EP 436316 and U.S. Pat. No. 5,019,370. Further, WO 9501966, EP 782563 and U.S. Pat. No. 5,817,873 read on compounds having e.g. 3 and 4 substituted triiodinated phenyl groups arranged linearly or around a central core. However, none of these proposed compounds are on the market.

Hence there still exists a desire to develop contrast agents that solves one or more of the problems discussed above. Such agents should ideally have improved properties over the soluble iodine containing compounds in one or more of the following properties: renal toxicity, osmolality, viscosity, solubility, injection volumes/iodine concentration and attenuation/radiation dose.

SUMMARY OF THE INVENTION

The present invention provides compounds useful as contrast media having improved properties over the known media with regards to at least one of the following criteria osmolality (and hence the renal toxicity), viscosity, iodine concentration and solubility. The contrast media comprises iodine containing contrast enhancing compounds where iodine containing compounds are chemical compounds containing a cyclopropane scaffolding moiety allowing for the arrangement of three iodinated phenyl groups bound to thereto. The iodine containing contrast enhancing compounds can be synthesized from commercially available and relatively inexpensive starting materials. The invention is further described in the attached claims.

DETAILED DESCRIPTION OF THE INVENTION

The contrast media comprises iodine containing contrast enhancing compounds of formula (I)

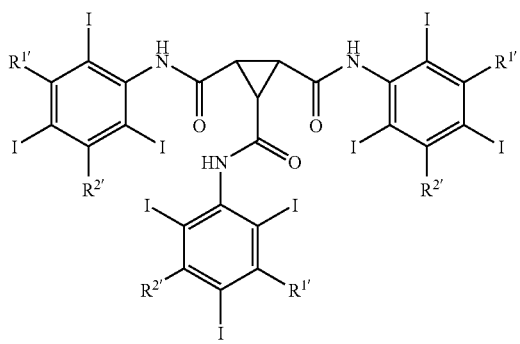

Formula (I)

wherein each $R_1'$ and $R_2'$ are the same or different and denote a hydrogen atom or a non-ionic hydrophilic moiety, provided that at least one of the $R_1'$ and $R_2'$ groups represent a non-ionic hydrophilic moiety, and salts or optical active isomers thereof.

The central cyclopropane moiety exert certain constrains on the structure of the compound of formula (I) e.g. by locking the iodinate phenyl groups in specific positions relative to each other and to the central cyclopropane moiety. Hence, the diameter and the molecular volume of the compound of formula (I) will be relatively small and the compound will consume a compact 3-dimensional configuration. Further, if the compounds can exist in isomeric forms, they should preferably be locked into one isomeric form and preferably the isomeric form with the smallest diameter, provided that the solubility of this isomer is satisfactory. The hydrophilic $R_1'$ and/or $R_2'$ groups present their hydrophilic groups at the surface of the molecule of formula (I) and contributing to the hydrophilic properties of the compound.

The hydrophilic moieties $R_1'$ and $R_2'$ may be any of the non-ionizing groups conventionally used to enhance water solubility. Suitable groups include straight chain or branched chain $C_{1-10}$alkyl groups, preferably $C_{1-5}$alkyl groups, optionally with one or more $CH_2$ or CH moieties replaced by oxygen or nitrogen atoms and optionally substituted by one or more groups selected from oxo, hydroxyl, amino or carboxyl derivative, and oxo substituted sulphur and phosphorus atoms. Particular preferred examples include polyhydroxyalkyl, hydroxyalkoxyalkyl and hydroxypolyalkoxyalky and such groups attached to the phenyl group via an amide linkage such as hydroxyalkylaminocarbonyl, N-alkyl-hydroxyalkylaminocarbonyl and bis-hydroxyalkylaminocarbonyl groups.

In a preferred embodiment the hydrophilic moieties $R_1'$ and $R_2'$ are selected from the groups listed below and preferably containing 1 to 6 hydroxy groups, more preferably 1 to 3 hydroxy groups. Examples of preferred groups comprise groups of the formulas:
—CONH—CH$_2$—CH$_2$—OH
—CONH—CH$_2$—CHOH—CH$_2$—OH
—CON(CH$_3$)CH$_2$—CHOH—CH$_2$OH
—CONH—CH—(CH$_2$—OH)$_2$
—CON—(CH$_2$—CH$_2$—OH)$_2$
—CONH$_2$
—CONHCH$_3$
—NHCOCH$_2$OH
—N(COCH$_3$)H
—N(COCH$_3$)C$_{1-3}$alkyl
—N(COCH$_3$)-mono, bis or tris-hydroxy C$_{1-4}$alkyl
—N(COCH$_2$OH)-hydrogen, mono, bis or tris-hydroxy C$_{1-4}$alkyl
—N(CO—CHOH—CH2OH)-hydrogen, mono, bis or trihydroxylated C$_{1-4}$alkyl.
—N(CO—CHOH—CHOH—CH2OH)-hydrogen, mono, bis or trihydroxylated C$_{1-4}$alkyl.
—N(COCH$_2$OH)$_2$
—CON(CH$_2$—CHOH—CH$_2$—OH)(CH$_2$—CH$_2$—OH)
—CONH—C(CH$_2$—OH)$_3$ and
—CONH—CH(CH$_2$—OH)(CHOH—CH$_2$—OH).

More preferably the $R_1'$ and $R_2'$ groups will be equal or different and denote one or more moieties of the formulas—CON(CH$_3$)CH$_2$—CHOH—CH$_2$OH, —CONH—CH$_2$—CHOH—CH$_2$—OH, —CONH—CH—(CH$_2$—OH)$_2$, —CON—(CH$_2$—CH$_2$—OH)$_2$, —CONH—CH$_2$—CHOH—CH$_2$—OH, —NHCOCH$_2$OH and —N(COCH$_2$OH)-mono, bis or tris-hydroxy C$_{1-4}$ alkyl.

Even more preferably all the $R_1'$ groups are equal and all the $R_2'$ groups are equal but may be different from $R_1'$ and they denote one of these moieties. All the $R_1'$ and $R_2'$ groups may also be equal and denote one of the preferred moieties and most preferred the moiety —CONH—CH$_2$—CHOH—CH$_2$—OH.

In the compounds of formula (I), the cyclopropane moiety which is the central scaffolding group exists in two isomeric forms, all syn and anti syn:

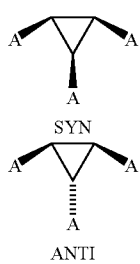

The figures above illustrate the two different isomers, syn and anti. The syn isomer has all substituents on the same side whereas the anti isomer has substituents on both sides of the central cyclopropane ring. The number of different isomers depends on the size of the ring. For a three-membered ring, only two isomers are possible. These are stereoisomers, a number of optical isomers are also possible and generally present.

The presence of many isomers increases the water solubility of a compound in that the compounds are to a greater or lesser extent hindered to form crystals and thereby to precipitate. The function is the same as the rotational isomers around the amide bond.

At an iodine concentration of 320 mg/ml, which is a common concentration for commercially available iodinated contrast media, the concentration of the compound of formula (I) will be approximately 0.28 M (Molar). The contrast medium will also be hypoosmolar at this iodine concentration, and this is an advantageous property with regards to the nephrotoxicity of the contrast medium. It is also possible to add electrolytes to the contrast medium to lower the cardiovascular effects as explained in WO 90/01194 and WO 91/13636.

Compounds of formula (I) also comprises stereoisomers and optical active isomers. Both enantiomerically pure products as well as mixtures of optical isomers are included.

The compounds of the invention may be used as contrast agents and may be formulated with conventional carriers and excipients to produce diagnostic contrast media.

Thus viewed from a further aspect the invention provides a diagnostic composition comprising a compound of formula (I) as described above together with at least one physiologically tolerable carrier or excipient, e.g. in aqueous solution for injection optionally together with added plasma ions or dissolved oxygen.

The contrast agent composition of the invention may be in a ready to use concentration or may be a concentrate form for dilution prior to administration. Generally compositions in a ready to use form will have iodine concentrations of at least 100 mg I/ml, preferably at least 150 mg I/ml, with concentrations of at least 300 mg I/ml, e.g. 320 mg I/ml being preferred. The higher the iodine concentration, the higher is the diagnostic value in the form of X-ray attenuation of the contrast media. However, the higher the iodine concentration the higher is the viscosity and the osmolality of the composition. Normally the maximum iodine concentration for a given contrast media will be determined by the solubility of the contrast enhancing agent, e.g. the iodinated compound, and the tolerable limits for viscosity and osmolality.

For contrast media which are administered by injection or infusion, the desired upper limit for the solution's viscosity at ambient temperature (20° C.) is about 30 mPas, however viscosities of up to 50 mPas and even up to 60 mPas can be tolerated. For contrast media given by bolus injection, e.g. in angiographic procedures, osmotoxic effects must be considered and preferably the osmolality should be below 1 Osm/kg $H_2O$, preferably below 850 mOsm/kg $H_2O$ and more preferably about 300 mOsm/kg $H_2O$.

With the compounds of the invention such viscosity, osmolality and iodine concentrations targets can be readily met. Indeed, effective iodine concentrations will be reached with hypotonic solutions. It may thus be desirable to make up the solution's tonicity by the addition of plasma cations so as to reduce the toxicity contribution that derives from the imbalance effects following bolus injection. Such cations will desirably be included in the ranges suggested in WO 90/01194 and WO 91/13636.

In particular, addition of sodium and calcium ions to provide a contrast medium isotonic with blood for all iodine concentrations is desirable and obtainable. The plasma cations may be provide in the form of salts with physiologically tolerable counterions, e.g. chloride, sulphate, phosphate, hydrogen carbonate etc., with plasma anions preferably being used.

The compounds of the general formula (I) can be synthesized by several synthetic pathways known to the skilled artisan from starting materials available in the market.

Hence, in one embodiment, cyclopropane-1,2,3-tricarboxylic acid, is prepared according to a literature method (J. Org. Chem. 1199-1202 (1965); J. Am. Chem. Soc. 89, 6318-27 (1967)). The cyclopropane-1,2,3-tricarboxylic acid is converted to cyclopropane-1,2,3-tricarboyl trichloride following the procedure described by A. Speziale, R. Lowell, J. E. Fedder; J. Org. Chem. 30, 1199 (1965)) using the literature method: P. A. Waitkus, E. B. Sanders, L. I. Peterson, G. W. Griffin; J. Amer. Chem. Soc. 89, 6318 (1967). The acid chloride is treated with an excess of a triiodinated $R_1'$ and $R_2'$ substituted anilines as illustrated below.

The manufacture of the triiodinated $R_1'$ and $R_2'$ substituted anilines are illustrated e.g. in EP 0108638 where a compound denoted compound A has a preferred structure. When the substituted aniline comprises reactive functions such as hydroxyl groups, these functions should be protected e.g. by acetylation and the protecting groups will be removed in an additional step.

The synthesis of compounds of formula (I) is illustrated in the following reaction scheme:

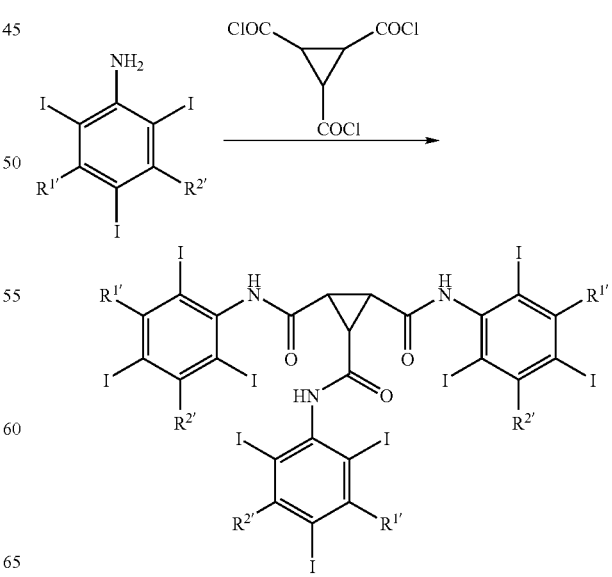

The synthesis will now be illustrated by the following non-limiting example:

EXAMPLE $N^1,N^2,N^3$-tris(3,5-bis(2,3-dihydroxypropylcarbamoyl)-2,4,6-triiodophenyl)cyclopropane-1,2,3-tricarboxamide a) 5-amino-$N^1N^3$-bis(2,3-diacetoxypropyl)-2,4,6-triiodobenzene-1,3-diamide 5-amino-$N^1,N^3$-bis(2,3-hydroxypropyl)-2,4,6-triiodobenzene-1,3-diamide (40.0 g, 0.057 mol) was suspended in pyridine (80 ml). With efficient stirring and cooling in an ice-water bath acetic anhydride (70 ml) was added dropwise. Stirring was continued for 24 h at ambient temperature. The solution was evaporated to an oil, which was dissolved in ethyl acetate (ca 0.5 liter). This solution was washed with diluted hydrochloric acid (0.1 M, 100 ml), water (2×200 ml), diluted sodium hydrogencarbonate solution (5%, 2×200 ml) and at last a saturated solution of sodium chloride (70 ml). The organic phase was filtered through a pad of alumina (h=10 cm, ø=8 cm). The solvent was evaporated to give a white crystalline compound. Yield: 49 g (99%). Analyzed by $^1$H NMR and LC-MS.

b) $N^1,N^2,N^3$-tris(3,5-bis(2,3-dihydroxypropylcarbamoyl)-2,4,6-triiodophenyl)cyclopropane-1,2,3-tricarboxamide Cyclopropane-1,2,3-tricarboyl trichloride is prepared from cyclopropane-1,2,3-tricarboxylic acid (A. Speziale, R. Lowell, J. E. Fedder; J. Org. Chem. 30, 1199 (1965)) using the literature method: P. A. Waitkus, E. B. Sanders, L. I. Peterson, G. W. Griffin; J. Amer. Chem. Soc. 89, 6318 (1967). The acid chloride is treated with 5 equivalents of 5-amino-$N^1,N^3$-bis(2,3-diacetoxypropyl)-2,4,6-triiodobenzene-1,3-diamide in dimethylacetamide. After stirring the solution for 3 days, water is added and the solution is extracted with ethyl acetate. The organic phase is washed with water, evaporated to dryness and the residue is purified by preparative HPLC. The purified product is then hydrolyzed by sodium hydroxide (24 equivalents) in a mixture of methanol and water. The final product is purified by preparative HPLC.

The invention claimed is:

1. A compound of formula (I)

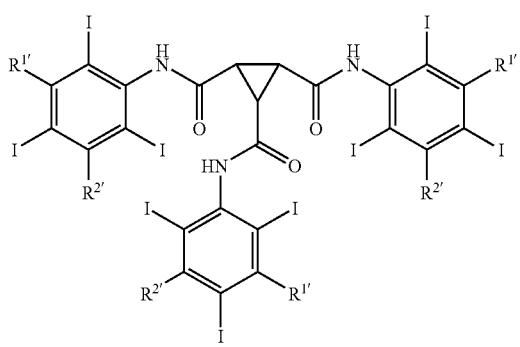

Formula (I)

wherein each $R_1'$ and $R_2'$ are the same or different and denote a hydrogen atom or a non-ionic hydrophilic moiety provided that at least one of the $R_1'$ and $R_2'$ groups represent a non-ionic hydrophilic moiety, and salts or optical active isomers thereof.

2. A compound as claimed in claim 1 wherein the hydrophilic moieties $R_1'$ and/or $R_2'$ denotes straight chain or branched chain $C_{1-10}$ alkyl groups, preferably $C_{1-5}$ alkyl groups, optionally with one or more $CH_2$ or CH moieties replaced by oxygen or nitrogen atoms and optionally substituted by one or more groups selected from oxo, hydroxyl, amino or carboxyl derivative, and oxo substituted sulphur and phosphorus atoms.

3. A compound as claimed in claim 1 wherein the hydrophilic moieties $R_1'$ and/or $R_2'$ consists of polyhydroxyalkyl, hydroxyalkoxyalkyl and hydroxypolyalkoxyalky groups.

4. A compound as claimed in claim 1 wherein the hydrophilic moieties $R_1'$ and/or $R_2'$ are selected from the group comprising of
—CONH—$CH_2$—$CH_2$—OH
—CONH—$CH_2$—CHOH—$CH_2$—OH
—CON($CH_3$)$CH_2$—CHOH—$CH_2$OH
—CONH—CH—($CH_2$—OH)$_2$
—CON—($CH_2$—$CH_2$—OH)$_2$
—$CONH_2$
—$CONHCH_3$
—$NHCOCH_2OH$
—N($COCH_3$)H
—N($COCH_3$)$C_{1-3}$alkyl
—N($COCH_3$)-mono, bis or tris-hydroxy $C_{1-4}$alkyl
—N($COCH_2OH$)-hydrogen, mono, bis or tris-hydroxy $C_{1-4}$alkyl
—N(CO—CHOH—CH2OH)-hydrogen, mono, bis or tri-hydroxylated $C_{1-4}$alkyl
—N(CO—CHOH—CHOH—CH2OH)-hydrogen, mono, bis or trihydroxylated $C_{1-4}$alkyl
—N($COCH_2OH$)$_2$
—CON($CH_2$—CHOH—$CH_2$—OH)($CH_2$—$CH_2$—OH)
—CONH—C($CH_2$—OH)$_3$ and
—CONH—CH($CH_2$—OH)(CHOH—$CH_2$—OH).

5. A compound as claimed in claim 4 wherein $R_1'$ and $R_2'$ are equal and denote the group of the formula
—CON($CH_3$)$CH_2$—CHOH—$CH_2$OH,
—CONH—$CH_2$—CHOH—$CH_2$—OH,
—CONH—CH—($CH_2$—OH)$_2$,
—CON—($CH_2$—$CH_2$—OH)$_2$,
—CONH—$CH_2$—CHOH—$CH_2$—OH,
—$NHCOCH_2OH$ and
—N($COCH_2OH$)-mono, bis or tris-hydroxy $C_{1-4}$alkyl.

6. A compound as claimed in claim 5 wherein $R_1'$ and $R_2'$ are equal and denote the group of the formula
—CONH—$CH_2$—CHOH—$CH_2$—OH.

7. A diagnostic agent comprising a compound of formula (I) as defined in claim 1.

8. A diagnostic composition comprising a compound of formula (I) as defined in claim 1 together with a pharmaceutically acceptable carrier or excipient.

9. An X-ray diagnostic composition comprising a compound of formula (I) as defined in claim 1 together with a pharmaceutically acceptable carrier or excipient.

10. A diagnostic agent and a diagnostic composition containing a compound of formula (I) as defined in claim 1 wherein both the diagnostic agent and diagnostic compositions are used in X-ray contrast examinations.

11. A method of diagnosis comprising administration of compounds of formula (I) as defined in claim 1 to a human or animal body, examining the body with a diagnostic device and compiling data from the examination.

12. A method of diagnosis on a human or non-human animal preadministered with compounds of formula (I) as defined in claim 1, comprising examining the body with a diagnostic device and compiling data from the examination.

13. A method of imaging, specifically X-ray imaging, comprising administration of compounds of formula (I) as defined in claim 1 to a human or animal body, examining the body with a diagnostic device and compiling data from the examination and optionally analysing the data.

14. A process for the preparation of compounds of formula (I) as defined in claim 1 comprising the steps of a) converting cyclopropane-1,2,3-tricarboxylic acid to cyclopropane-1,2,3-tricarboyl trichloride
b) treating the cyclopropane-1,2,3-tricarboyl trichloride with an excess of a triiodinated $R_1'$ and $R_2'$ substituted aniline.

* * * * *